United States Patent [19]

Baran et al.

[11] Patent Number: 4,511,662
[45] Date of Patent: Apr. 16, 1985

[54] SIMULTANEOUS ASSAY FOR T AND B LYMPHOCYTE POPULATIONS AND SUBPOPULATIONS

[75] Inventors: Madelyn M. Baran, Novato; Dennis M. Bleile, Emeryville, both of Calif.

[73] Assignee: Bio-Rad Laboratories, Inc., Richmond, Calif.

[21] Appl. No.: 389,838

[22] Filed: Jun. 18, 1982

[51] Int. Cl.$^3$ ............................................. G01N 33/54
[52] U.S. Cl. ..................................... 436/513; 436/519; 436/523; 436/531; 436/533; 436/534; 436/548
[58] Field of Search ............... 435/4, 7, 810; 436/513, 436/523, 524, 527, 528, 529, 530, 531, 533, 534, 548, 544, 824, 519

[56] References Cited

U.S. PATENT DOCUMENTS

| | | | |
|---|---|---|---|
| 3,088,875 | 5/1963 | Fisk | 435/7 |
| 3,853,987 | 12/1974 | Dreyer | 436/533 |
| 4,105,598 | 8/1978 | Yen et al. | 435/7 |
| 4,223,005 | 9/1980 | Teodorescu et al. | 435/7 |
| 4,254,096 | 3/1981 | Monthony et al. | 436/534 |
| 4,284,412 | 8/1981 | Hansen et al. | 436/548 |
| 4,361,549 | 11/1982 | Kung et al. | 435/7 |
| 4,361,550 | 11/1982 | Kung et al. | 435/7 |
| 4,363,799 | 12/1982 | Kung et al. | 435/7 |
| 4,364,932 | 12/1982 | Kung et al. | 435/7 |
| 4,364,937 | 12/1982 | Kung et al. | 435/7 |
| 4,381,295 | 4/1983 | Kung et al. | 435/7 |
| 4,419,444 | 12/1983 | Quash | 436/533 |

FOREIGN PATENT DOCUMENTS 45103 2/1982 European Pat. Off. ............ 436/533

OTHER PUBLICATIONS

Mirro et al., J. Immunol. Methods, 47, 39–48, (1981).
Parish et al., J. Immunol. Methods, 53: 367–372, (1982).
Sevier et al., Clin. Chem., 27(6), 1109, Jun. (1981).
Identifying Human Lymphocyte Subpopulations and Assaying of Human Neutrophil Function (Reprints from Bio-Rad Laboratories).
The First Lymphochrome ™ B-Lymphocyte Test (Sigma Chemical Corp., 1 pg. brochure), (1980).
T & B Lymphocyte Identification with Monoclonal Antibodies–Hybritech T & B Cell Reagent Set from Hybritech Inc., (1981), (4 pgs.).
Kallestad Laboratories, Inc.–Kallestand Announces Development of Cellular Immunology Kits (2 pg. article).
Hudson and Hay–"Practical Immunology" Blackwell Scientific Publications, Second Edition.
Sigma Technical Bulletin #95, "An Immunoenzymatic Technic for Detecting Surface Immunoglobulins of Mature B-Lymphocytes, (Nov. 1980).

*Primary Examiner*—Esther M. Kepplinger
*Attorney, Agent, or Firm*—Townsend & Townsend

[57] ABSTRACT

An assay for simultaneously determining the ratio of B cells and T cells to the total cell population and subpopulations thereof present in a lymphocyte population utilizes excess amounts of B cell binding protein and T cell binding protein bound to solid phase particles. By exposing the particles to the lymphocyte population, rosettes are formed which may be visually distinguished and counted under a microscope, yielding the proportions of B cells and T cells, including any subpopulations for which a specific label was provided. Macrophages may be identified by their ability to ingest the particles.

26 Claims, No Drawings

SIMULTANEOUS ASSAY FOR T AND B LYMPHOCYTE POPULATIONS AND SUBPOPULATIONS

BACKGROUND OF THE INVENTION

1. Field of the Invention

The present invention relates generally to an assay for simultaneously determining the presence of T cells and B cells in a biological specimen, and more particularly, to an immunoassay for determining the relative amounts of T and B cells and subpopulations thereof by specifically labeling said cells with differentiable particles and counting the particles under a microscope.

In vertebrates, including man, T and B cells form the two primary lymphocyte populations. Upon stimulation with antigen, B cells differentiate into plasma cells which secrete antibodies specific to the antigen. The role of T cells is less well defined, although it is clear that they mediate cellular immune responses such as delayed hypersensitivity, immune surveillance and graft rejection. Certain T cell subpopulations also play a role in regulating the B cell response to antigens.

In normal individuals, the lymphocyte population in the peripheral blood comprises from about 70 to 80 percent T cells and from about 10 to 20 percent B cells with the remaining cells referred to as "null" cells. The determination of the relative number of T and B cells is clinically important in diagnosing a wide variety of immunologically-mediated diseases, including lymphomas, lymphocytic leukemias and various immunodeficiency diseases, such as congenital sex-linked agammaglobulinemia. The determination is also useful in evaluating immunocompetence and mechanisms of tissue damage in autoimmune diseases, such as systemic lupus erythematosus.

The T cell and B cell populations may further be divided into subpopulations distinguished by the presence of characteristic antigens on the cell surface membrane. The primary subpopulations of T cells are the helper ($T_H$) and suppressor ($T_S$) cells which function in humoral immune response. The primary B cell subpopulations correspond to the classes of immunoglobulin (Ig) present on the cell surface and produced by the plasma cell after stimulation. Determination of the relative amounts of the subpopulations of both B cells and T cells also promises to have clinical importance.

It is thus useful and desirable to provide a convenient and accurate method for determining the relative amounts of T cells and B cells and subpopulations thereof in a biological sample, such as human blood.

2. Description of the Prior Art

Heretofore, human B cells have been identified based on the presence of membrane-bound immunoglobulin. Typically, labeled anti-(human immunoglobulin) antibody is used to separate or otherwise identify the B cell population. The use of polyclonal anti-(human immunoglobulin) antibody coupled to polyacrylamide beads is discussed in Jabs, et al., "Identifying Human Lymphocyte Subpopulations," Lab. Manag., (January, 1980). Such beads are available from Bio-Rad Laboratories, Richmond, Calif. Enzyme-labeled goat anti-(human immunoglobulin) antibody is described in Technical Bulletin No. 95, Sigma Chemical Company, St. Louis, Mo.

T cells have been conventionally identified by their ability to spontaneously bind with sheep red blood cells to form "rosettes" visible under an ordinary light microscope. A description of this technique is found in Hudson, et al, "Practical Immunology," Blackwell Scientific Publications, Oxford, pp. 301–302 (1980).

Commercial kits are presently available for the assay of the B cell and T cell populations in human blood. One such kit, available from Kallestad Laboratories, Inc., Austin, Tex., utilizes labeled anti-(human immunoglobulin) antibody for detecting B cells and sheep red blood cells for identifing T cells in separate steps. Another kit, identified as the "T & B Cell Reagent Set," manufactured by Hybritech, Inc., La Jolla, Calif., combines labeled anti-T cell antibody (monoclonal) and labeled anti-B cell antibody (monoclonal) for the enumeration of T and B cells using fluorescent microscopy.

SUMMARY OF THE INVENTION

The present invention provides a method and kit for the simultaneous determination of the relative amounts of B cells and T cells and subpopulations thereof in a lymphocyte population, usually derived from the blood or bone marrow.

The kit includes at least two classes of visually distinguishable labels. The first class usually comprises binding protein which is specific for B cells and which is immobilized on insoluble support particles, typically small polymeric particles in the size range from about 0.5 to 20 microns. The second class usually comprises binding protein which is specific for T cells and which is immobilized on particles which are usually, but need not be, similar to those of the first class. Either before or after immobilization of the binding proteins, at least one of the two classes of label is "marked" to allow the labels to be visually distinguished under a microscope. Typically, this is accomplished by dyeing the support particles of one or both of the classes prior to or after attachment of the binding protein.

The method is not limited to distinguishing B cells from T cells and can be extended to distinguising among the various subpopulations of B cells and T cells. In general, the method can be applied to distinguish any subpopulation which is characterized by the presence of a unique antigenic site on the cell surface membrane and for which a specific binding protein exists or can be obtained. Visually distinguishable labels can then be produced in the manner just described.

In performing the method, the lymphocyte population must first be isolated. In the case of blood lymphocytes this is usually accomplished by density gradient centrifugation. After isolation, the lymphocyte population is simultaneously exposed to both the B cell and T cell labels (including labels specific for any subpopulations) for a sufficient time to form "rosettes" with all the B cells and T cells. The rosettes may be visually distinguished under a microscope, and a count of the B cell rosettes and T cell rosettes directly indicates the relative number of B cells and T cells in the sample. Macrophages, a contaminant of the lymphocyte preparation, may be identified by their ability to ingest the polymeric beads which are part of the kit.

DESCRIPTION OF THE PREFERRED EMBODIMENT

The present invention will be described in detail for the exemplary situation where the relative amounts of B cells and T cells are to be determined. In that case, only two labels, specific for B cells and T cells respectively, are required. It is to be understood that the present invention encompasses the method where one or more B cell or T cell subpopulations are to be simultaneously determined by providing label specific for the cells of the particular subpopulations.

Materials

1. Particle Supports

The particle supports can be composed of a wide variety of materials and need not be a single material. The material must be capable of coupling the binding protein as well as a dye. A third criterion is that the material must be capable of forming small particles, in a range of from 0.5 to 20 microns, which are useful in the method of the present invention.

The materials of choice include a wide variety of polymeric materials, such as polyethylene, polypropylene, polyvinyl compounds such as polyvinylchloride, polyacrylonitrile, polyacrylate, polymethacrylate and copolymers thereof, polystyrene, nylon, polyterephthlate, cellulose and the like. The group includes naturally occuring polymers, particularly modified naturally occurring polymers and synthetic addition and condensation polymers. Also useful are cross-linked dextran particles and inorganic materials such as various glasses which may be derivatized to conjugate the binding protein as well as the dye.

Preferred are hydrolyzed cross-linked polyacrylamide particles which in the hydrolized form have a particle size of 0.5 to 20 microns, usually about 5 to 15 microns. It is desirable that the size of the particle correspond generally to the size of the lymphocytes, i.e., approximately 7 to 10 microns, preferably having a particle size distribution (90%) centered about 8 to 9 microns. Suitable beads are designated as P-6 Microbeads®, available from Bio-Rad Laboratories, Richmond, Calif. The P-6 Microbeads® should be sorted by size prior to use to obtain the desired particle size distribution.

Immobilization of the binding protein can be achieved by a variety of known techniques. Depending on the material as well as on the particular binding protein, physical absorption or adsorption could be employed. Preferably, however, the binding protein is covalently bonded to the particle. For example, carboxyl groups on the particle surface can be made reactive with the available amino groups on the binding protein. This is particularly useful when the dye is also bound to the bead through amino groups, as is the preferred technique in the present invention. Extensive literature is available concerning the binding of proteins and other molecules to surfaces employing activated carboxylic acids, carbodiimides, imido esters, active alkyl halides, etc., to form amido, amidine or amino linkages.

The preferred P-6 Microbeads® may be activated by hydrolyzing in 2N sodium hydroxide. When the beads are to be dyed, they should be hydrolyzed to a binding capacity of at least six meq (milliequivalents)/gm, typically requiring three days at room temperature. When the beads are not to be dyed, a binding capacity of 3 meq/gm is sufficient, requiring hydrolysis for only 18 to 24 hours at room temperature. The hydrolyzed P-6 Microbeads® are then equilibrated against coupling buffer prior to incubation with the binding protein and dyeing, as will now be described.

2. Preparation of B Cell Labels

The present invention requires the immobilization of B cell binding protein (i.e., proteins capable of specifically binding to B cells) on solid phase particles, typically comprising insoluble beads as just described. B cell binding protein will usually be either monoclonal or polyclonal anti-(human immunoglobulin) antibody. Polyclonal anti-(human immunoglobulin) antibody is available from a number of sources, including Accurate Chemical and Scientific Corporation, Westbury, N.Y., [rabbit anti-(human immunoglobulin) antiserum manufactured by Dako, Denmark] and Miles Laboratories, Elkhart, Ind. [goat anti-(human immunoglobulin) antiserum]. When it is desired to further distinguish between particular B cell subpopulations, it will of course be necessary to utilize an antibody specific for the particular class of immunoglobulin, i.e., IgG, IgM, IgA, IgD and IgE, present on the B cell surface membrane.

Using the activated P-6 Microbeads® described above, antibody can be covalently bound as follows. An immunoglobulin fraction of rabbit anti-(human immunoglobulin) antiserum is dialyzed overnight in the cold against coupling buffer (e.g., 0.003M Na phosphate, pH 6.3) and a predetermined amount of immunoglobulin is then added to the activated beads and the pH adjusted in the range from 6.2 to 6.4. After thirty minutes at room temperature, EDAC [1-ethyl-3(3-dimethylaminopropyl) carbodiimide-HCl] is added and the coupling reaction is allowed to continue for about 5 to 15 hours in the cold. The amount of immunoglobulin reacted is not critical, although it is necessary that sufficient anti-Ig antibodies be coupled to the beads to assure their ability to bind B cells. In the above procedure, an immunoglobulin ooncentration of from 8 to 48 mg immunoglobulin per gram of bead has been found suitable.

3. Preparation of T Cell Labels

The preferred T cell binding protein (i.e., protein capable of specifically binding to T cells) is monoclonal anti-(T cell) antibody, such as T101 obtained from the Murine Hybridoma Cell Line, ATCC aquisition number CRL-8023. Freshly isolated hybridoma cultures may be grown in vitro and the monoclonal antibody recovered from the supernatant fluid.

Alternatively, large amounts of hybridoma-derived antibody may be produced by injecting the tumorogenic hybridoma line into histocompatible (or immunoincompetent) mice. The procedure is well known in the art and described in Hudson, et al, Id, at pages 320–321.

Ascitic fluid obtained from the mice often contains up to 10 mg/ml of antibody, but also contains other proteins. The antibodies may be purified by affinity chromatography on immobilized protein A, such as Protein A-Sepharose® CL4B (Pharmacia Fine Chemicals, Piscataway, N.J.). An ammonium sulfate fraction of the ascitic fluid is dialyzed against buffer (pH 8.0) and is applied to the column. After washing with 0.1M phosphate buffer (pH 8.0), the monoclonal antibody is eluted with 0.1M Na citrate (pH 3.0) and dialyzed overnight in the cold against phosphate buffered saline (PBS) at pH 7.2.

The purified monoclonal antibody may be coupled to hydrolyzed P-6 Microbeads, prepared as previously described. After dialyzing against coupling buffer, the purified monoclonal antibody is added to the hydrolyzed P-6 Microbeads® at a concentration of from 5 to 40 mg antibody/gm microbeads, preferably 10 mg/gm, and pH is adjusted in the range from 6.2 to 6.4. After thirty minutes at room temperature, EDAC is added to the mixture to a final concentration in the range from 0.2 to 0.5 mg/g. The pH is adjusted in the range from 6.2 to 6.4 and the reaction is allowed to continue for a period from about 5 to 15 hours in the cold. The beads are kept in suspension, typically with an end-over-end rocker or an overhead stirring device.

After incubation, the beads are washed three times with a solution of 0.1% bovine serum albumin (BSA) in PBS, three times with a solution of 1.4M NaCl and 0.1% BSA in PBS, and three times with 0.1% BSA in PBS.

4. Dyeing the Labels

The labels must be marked in some convenient manner so that the B cell beads may be visually distinguished from the T cell beads when viewed under a microscope. Most conveniently, this is accomplished by dyeing one or both of the B cell and T labels, usually by covalently attaching a dye which is visible under a light microscope. In the past, it has been difficult to discern under a light microscope whether or not a small particle, such as the polymeric particles employed in the present invention, have been dyed. The specific procedure now described overcomes this problem.

In the preferred embodiment, the B cell labels are dyed after the particles have been conjugated to anti-(human immunoglobulin) antiserum. The method would work equally well, however, if the T cell labels were dyed. Moreover, the label particles could be dyed prior to coupling the binding protein so long as sufficient activated sites remained on the particle for coupling the binding protein. When dyeing the labels after binding protein conjugation, it is desirable to limit the concentration of dye to prevent inactivation of binding protein.

When distinguishing only B cells and T cells (and no subpopulations) it is preferable to dye only one of the two labels since it is easier to distinguish between "dyed" and "not dyed" than between two different colors. When assaying the subpopulations as well, however, it is necessary to dye more than one of the labels so that each particular label is distinguishable.

The particles may be dyed directly following conjugation of the receptor by centrifuging the beads, decanting the supernatant, and resuspending the beads in a solution of 0.2 weight percent Bismark Brown Y (see, Welcher, "Organic Analytical Reagents," Van Norstrand Co., N.Y., 1948) in coupling buffer, one volume of beads to about eight volumes of dye. After 30 minutes, EDAC (250 mg/gm beads) is added and the reaction is allowed to proceed for from 5 to 15 hours in the cold. The beads are then washed with PBS (0.1% BSA) and PBS (1.4M NaCl, 1% BSA) as set forth previously.

The above procedure employing EDAC to couple the dye to hydrolyzed beads is applicable to any dye having free amino groups. The dye will preferably have a molecular weight below 5000, usually below 1000, so that it may react with hydrolyzed groups interior to the bead and unavailable to the binding proteins.

Although the preferred embodiment utilizes labels which are dyed to be distinguishable under a visible light microscope, the invention extends to fluorescent dyes which may be visually distinguished under a fluorescent microscope, as well as to enzyme systems which generate chromogens at or near the surface of the beads, and the like.

5. Preparation of Reagents

In order to assure that sufficient labels will be available to react with every B and T cell in the sample, it is necessary that the label/cell ratio be maintained in excess, typically in the range from about 50 to 100 labels for each B and T cell. The absolute concentration of markers in the reagent solution added to the sample will, of course, depend on the sample size as well as on the concentration of B and T cells in the sample.

Method

1. Isolation of the Lymphocyte Population

The method of the present invention may be practiced on any lymphocyte population isolated from a vertebrate. For example, lymphocyte suspensions may be prepared from various organs such as spleen, lymph nodes, bursa or thymus by teasing the organs apart with forceps so that cells are forced into tissue culture medium, or by teasing the organ with fine forceps over a fine wire mesh or tea strainer. Specific methods for preparing such suspensions are discussed in Hudson, et al, Id, at p. 19. The particular B cell and T cell binding proteins disclosed hereinabove are, of course, specific for the human lymphocyte population and other binding protein will be required for species other than man.

Usually, the method of the present invention will be applied to the human blood lymphocyte population which may be obtained from a blood sample. In that case, it is necessary to separate or remove the red blood cells from the blood prior to the assay. Many different methods are available for achieving such a separation. Preferred is differential centrifugation on a density gradient which is rapid and yields a high purity lymphocyte preparation.

The procedure for density gradient centrifugation is as follows. Appropriately diluted blood (3–5 ml) is layered onto a density gradient formulated such that only the red cells and granulocytes form a pellet. Suitable density gradient preparations include Ficoll-Paque ® (Pharmacia Fine Chemicals, Piscataway, N.J.) and Histopaque ®-1077 (Sigma Chemical Company, St. Louis, Mo.). The sample is then centrifuged at 400 g for 20 minutes at 18° to 20° C. The lymphocytes with contaminating macrophages appear at the plasma/density gradient interface. Lymphocytes are then washed from one to three times with balanced salt solution and pelleted by centrifugation at from 100 to 150 g for from 5 to 10 minutes at 18° to 20° C. The separated cells contain the lymphocytes (B cells, T cells and "null" cells) as well as macrophages, all of which are indistinguishable under a light microscope.

As an alternative to density gradient centrifugation, the red blood cells may be removed from the blood sample by first lysing the red cells in the whole blood and then washing away the lysed cells. While this method is functional, the lymphocytes are contaminated with granulocytes (another type of white blood cell). Although most granulocytes are phagocytic and do not significantly alter the T-B cell ratio, their presence decreases the absolute concentration of lymphocytes requiring a longer period to count a sufficient number of lymphocytes to provide a statistically reliable measure of the ratio.

2. Identification of B Cells, T Cells and Macrophages

After isolation, the lymphocyte population may be incubated with the B cell and T cell labels at a concentration (labels/cell) of 10:1 having no upper limit, preferably at least 50:1 with an upper limit of 500:1. The labels will form rosettes by binding about the periphery of the homologous cell (B or T or a particular subpopulation thereof, depending on the specificity of the label) in a manner similar to the rosettes formed by sheep red blood cells about T cells. The labels which form rosettes may then be counted under a visible light microscope, with the B cell rosettes distinguished by their darker color resulting from the dye. A count of at least 100, preferably 200, rosettes is then made to determine the ratio of B cells and T cells to the total cell population.

Incubation is carried out at room temperature for a period of at least 5 min., preferably 30 min. or longer. The longer incubation period allows macrophage ingestion of both the B cell and T cell labels. Macrophage ingestion is clearly visible under the microscope and allows differentiation of the remaining lymphocyte population ("null" cells) and the macrophages, which are otherwise indistinguishable.

Experimental Results

B cell and T cell markers were prepared using P-6 Microbeads®, T101 monoclonal anti-(T cell) antibody and polyclonal anti-(human immunoglobulin) antibody (Dako), as described previously.

A sample of normal blood (4 ml) was diluted (1:1) with PBS, layered onto Ficoll-Paque® (3 ml), and centrifuged at 400 g for 20 min. The white cell layer was removed and washed one time with PBS (0.1% BSA) and incubated for 30 min. at 37° C. to release cytophilic Ig from the lymphocytes. After washing twice with PBS, the cell concentration was adjusted to approximately $10^7$ cells/ml. The cells (100 μl) and labels (200 μl of both labels, each at approximately the same concentration) were placed in a test tube and incubated for 30 min. at room temperature. After centrifuging for 3 min., the cells were resuspended in PBS, 100 μl of 0.03% trypan blue in PBS was added, and one drop of the suspension placed on a microscope slide. Rosettes (200) were randomly counted and the number of B cell rosettes and T cell rosettes recorded. Only viable cells (i.e., those which excluded the trypan blue dye) were counted. The results indicated 75.8% T cells, 13.3% B cells and 7.7% null cells. These results fall well within the range of expected results. Macrophages with intracellular beads were also clearly identifiable.

The same protocol was applied to a sample of blood from a patient who was diagnosed as having chronic lymphocytic leukemia. In this case, the following results were obtained: 21% T cells, 71% B cells and 8% null cells.

Although the best mode contemplated for carrying out the present invention has been herein shown and described, it will be appreciated that variations and modifications may be made without departing from what is regarded to be the subject matter of the present invention.

What is claimed is:

1. A method for simultaneously determining the relative number of B cells and T cells in a lymphocyte population of a vertebrate, said method employing (1) B cell labels comprising insoluble polymeric particles having a size in the range from 5 to 15 microns bound to B cell binding proteins and (2) T cell labels comprising insoluble polymeric particles having a size in the range from 5 to 15 microns bound to T cell binding protein, at least one of said B cell and T cell labels being covalently coupled to a dye which imparts a color to the particle which is visible under a light microscope, said method comprising:

incubating the lymphocyte population simultaneously with the B cell labels and T cell labels for a time sufficient for all of the B cells and T cells to specifically form rosettes with the corresponding label; and counting the number of B cell rosettes and T cell rosettes under a light microscope.

2. A method as in claim 1, wherein the lymphocyte population is isolated from blood by density gradient centrifugation.

3. A method as in claim 1, wherein the lymphocyte population is isolated from blood by lysing the red blood cells and removing the lysed cells.

4. A method as in claim 1, wherein the lymphocyte population is isolated from bone marrow.

5. A method as in claim 1, wherein the B cell label comprises anti-(human immunoglobulin) antibody covalently bonded to the polymeric particle.

6. A method as in claim 1, wherein the T cell label comprises monoclonal anti-(T cell) antibody covalently bonded to the polymeric particle.

7. A method as in claim 1, wherein the polymeric particles are polyacrylamide.

8. A method as in claim 1, further including the step of counting the macrophages by observing the number of cells which have ingested beads.

9. A method as in claim 1, wherein said B cell label includes at least two classes specific for different subpopulations of B cells wherein the different classes of labels are dyed different colors, the method further comprising counting the number of rosettes related to each of said subpopulations.

10. A method as in claim 9, wherein said subpopulations of B cells are selected from B cells displaying surface IgG, IgM, IgA, IgD and IgE.

11. A method as in claim 1, wherein said T cell label includes at least two classes specific for different subpopulations of T cells wherein the different classes of labels are dyed different colors, the method further comprising counting the number of rosettes related to each of said subpopulations.

12. A method as in claim 11, wherein said subpopulations of T cells are selected from $T_H$ cells and $T_S$ cells.

13. A method as in claim 1, wherein the dye is Bismark Brown Y coupled to the dyed label through an amino group on the dye.

14. A kit for use in an immunoassay for determining the relative number of B cells and T cells present in an isolated human lymphocyte population, said kit including:

B cell label comprising anti-(human immunoglobulin) antibody covalently bonded to insoluble polymeric particles having a size in the range from 5 to 15 microns; and T cell label comprising anti-(T cell) antibody covalently bonded to insoluble polymeric particles having a size in the range from 5 to 15 microns, where at least one of said B cell label and T cell label has been covalently coupled to a dye so that the markers may be distinguishable under a light microscope.

15. A kit as in claim 14, wherein the B cell label and T cell label are lyophilized.

16. A kit as in claim 14, wherein the B cell label and T cell label are present in phosphate buffered saline solution.

17. A kit as in claim 14 wherein the anti-(human immunoglobulin) antibody is polyclonal.

18. A kit as in claim 14, wherein the anti-(human immunoglobulin) antibody is monoclonal.

19. A kit as in claim 14, wherein the anti-(T cell) antibody is polyclonal.

20. A kit as in claim 14, wherein the anti-(T cell) antibody is monoclonal.

21. A kit as in claim 14, wherein the dye is Bismark Brown Y and is covalently attached to the dyed label through an amino group on the dye.

22. A kit as in claim 14, wherein the insoluble particles used for the T cell label are formed from a different material than those of the B cell label.

23. A kit as in claim 14, wherein the insoluble particles for both the B cell label and T cell label are formed from the same material.

24. A kit as in claim 23, wherein the insoluble particles are polyacrylamide.

25. A kit as in claim 14, wherein the B cell label includes at least two classes specific for different subpopulations of B cells, said subpopulations being selected from B cells having IgG, IgA, IgM, IgD and IgE present on the cell surface.

26. A kit as in claim 14, wherein the T cell label includes two classes specific for the $T_H$ and $T_S$ subpopulations respectively.

* * * * *